United States Patent [19]

Tans et al.

[11] Patent Number: 4,630,923

[45] Date of Patent: Dec. 23, 1986

[54] FIBEROPTIC SPECTROPHOTOMETER

[75] Inventors: Petrus P. Tans; Daniel A. Lashof, both of Berkeley, Calif.

[73] Assignee: The United States of America as represented by the United States Department of Energy, Washington, D.C.

[21] Appl. No.: 697,824

[22] Filed: Feb. 4, 1985

[51] Int. Cl.$^4$ .................. G01J 3/44; G01N 21/65
[52] U.S. Cl. ....................................... 356/301
[58] Field of Search ............... 356/301, 319, 323, 325, 356/417; 372/107

[56] References Cited

U.S. PATENT DOCUMENTS

| | | |
|---|---|---|
| 3,521,958 | 7/1970 | Treharne . |
| 3,579,140 | 5/1971 | Anderson et al. ............... 372/107 |
| 3,825,335 | 7/1974 | Reynolds ............................. 355/1 |
| 3,874,780 | 4/1975 | Love . |
| 3,885,879 | 5/1975 | Louder et al. ..................... 250/227 |
| 3,901,581 | 8/1975 | Thiel . |
| 3,924,949 | 12/1975 | Honkawa et al. . |
| 4,027,153 | 5/1977 | Käch ................................. 250/227 |
| 4,063,822 | 12/1977 | de Jong et al. ................... 356/53 |
| 4,125,329 | 11/1978 | French et al. .................... 356/405 |
| 4,165,180 | 8/1979 | Failes .............................. 356/310 |
| 4,198,118 | 4/1980 | Porter ............................. 350/96.16 |
| 4,240,694 | 12/1980 | Pan ................................. 350/96.16 |
| 4,285,570 | 8/1981 | Minemura et al. ............... 350/96.18 |
| 4,299,485 | 11/1981 | Barlow et al. ................... 356/307 |
| 4,305,641 | 12/1981 | Witte .............................. 350/96.15 |
| 4,305,663 | 12/1981 | Perkins et al. ................... 356/323 |
| 4,318,586 | 3/1982 | Coyne ............................. 356/96.16 |
| 4,357,673 | 11/1982 | Willis et al. ..................... 356/323 |

FOREIGN PATENT DOCUMENTS 128886 10/1980 Japan ................................. 372/107

OTHER PUBLICATIONS

Weber et al, *Journal of the Optical Society of America*, vol. 57, No. 1, Jan. 1967, pp. 19–28.
Press Release, issued Nov. 23, 1983, by Lawrence Berkeley Laboratory, describing the Principles of Raman-Scatter Spectroscopy.

Primary Examiner—F. L. Evans
Attorney, Agent, or Firm—Charles E. Lykes, Jr.; Roger S. Gaither; Judson R. Hightower

[57] ABSTRACT

A device for determining the relative composition of a sample of a gas by comparison of the Raman-scattered light of the sample with that of a known gas comprising: a means for passing a single light source through the unknown and the known gases, choppers to alternate the Raman-scattered light into a common light detection and measuring system, optical fiber networks for spatially mixing the resulting Raman scattered light from each sample and directing the mixed light to selective detectors, and a compiler to record the light intensity of each wavelength of Raman-scattered light as a function of the sample from which it originated.

16 Claims, 6 Drawing Figures

FIBEROPTIC SPECTROPHOTOMETER

BACKGROUND OF THE INVENTION

The invention described herein arose in the course of, or under, Contract No. DE-AC03-76SF00098 between the United States Department of Energy and the University of California.

The invention relates to spectrophotometers, and more particularly to an improved spectrophotometer designed to compare Raman-scattered light from similar gas samples utilizing a fiberoptic system which allows simplification of the electronic and data compiling circuitry present in the prior art.

A number of devices exist to spectroscopically examine the chemical or physical properties of gases. Most such devices, a few of which will be described below, incorporate comparison of two beams (one being an analyzing beam and the other a reference beam), or the comparison of an obtained value with that of a known value, in order to achieve their result. A problem inherent in all of these systems however, is the need to identify and remove experimental errors in the data which may arise from differences either in the paths of the respective beams or in the light detection systems. Another problem inherent in Raman-scattering analysis systems is the weak nature of Raman-scattered light, particularly when analyzing less dense gases with commercially available lasers.

An example of a system designed to eliminate these kinds of experimental errors in spectrophotometer devices is provided in U.S. Pat. No. 4,357,673, issued Nov. 2, 1982 to Willis et al., which teaches a device which, when performing spectrographic comparisons of a sample with a reference, is designed to provide measurements free of errors caused by inconsistencies in the optical source or the optical detectors. It comprises a means of recording measurements of sample, reference, and background data along with a data processing unit to quickly compute average values and average variances, and then to combine these with the background values and solve for measurements free of experimental error. However, the system requires highly sophisticated data processing in order to eliminate experimental errors.

U.S. Pat. No. 3,521,958, issued July 28, 1970 to Treharne, describes a spectrophotometer designed to split the output of a monochromatic beam into two beams, sending one beam through the reference and the other beam through the sample for eventual comparison with each other. Treharne teaches the elimination of experimental error by several methods. One involves modulating both beams at different, but high frequencies (100–160 kc), so that a photomultiplier tube can readily distinguish them. Additionally, a circuit is provided to steady the output of the photomultiplier tube from the reference beam so that these readings will be free from variations in beam intensity. In another embodiment, the beams are modulated at the same frequency, but phase-shifted for distinction. Again however, the circuit is provided to steady the output from the reference beam to free the data from variations in beam intensity.

Both of the systems just described depend upon complex electronics and data processing in order to produce reliable results.

Major problems encountered by prior spectrophotometer art, as has been shown, arise from the need to eliminate or compensate for variances in light source intensity, transmission paths, and signal detection. Fiber optics provide a versatile and reliable means of delivering light signals to a specific point in a controlled manner. In other fields, fiber optic light transmission has been successfully used to solve such problems.

U.S. Pat. No. 4,305,646, issued Dec. 15, 1981 to Witte, teaches the use of an optical mixing element in order to evenly distribute data signals from a number of sources to any number of computer processing units or compilers. It comprises a mixing bar with input and output optical fibers. Into one end of the bar is fed data from a number of sources, each through a separate input optical fiber. These input fibers are "merged" both together and into the bar by both tapering the bar outward at the ends and fusing the fibers together into the tapered ends. The light signals then pass through the bar with only small losses as total internal reflection traps the light signals down the length of the bar. While in the bar, light from the different sources is thoroughly mixed. At the output end of the bar, the mixed light passes through another tapered zone, another area of fused fibers and then out through individual output optical fibers to their separate destinations. The light in each output fiber, however, is a composite of the light from each of the input fibers.

SUMMARY OF THE INVENTION

The present invention allows for accurate spectrophotometric comparison of the Raman scattering from a sample gas with the Raman scattering from a known gas via a novel fiberoptic network and eliminates the need for complicated electronic or optical circuit balancing, control, or error compensation circuitry. Additionally the invention provides a means of obtaining an adequately strong Raman-scattered light signal from gas samples by providing a novel laser cavity design, allowing the gas samples to placed within the laser cavity and stabilizing the beam through them.

The laser cavity is split into two regions, one of which houses the plasma discharge and produces the laser power and the other of which is adapted to house tubes containing the gas samples within the confines of the cavity. The laser beam may be separately monitored and moved through each of these regions of the laser cavity.

Light from a single laser source is beamed simultaneously through samples of a reference gas mixture whose constituency is known to a high degree of accuracy, and a similar, but unknown, gas mixture. As the laser beam passes through them each constituent element within a given gas sample emits Raman-scattered light of a different wavelength resulting in a composite set of bands of Raman-scattered light proportionately representative of the constituents within that mixture.

Raman-scattered light from the known and unknown gas mixtures is then alternately passed through a fiberoptic network. While in this network the various wavelengths of light present within a given sample are spatially mixed together. This is done by feeding the light into a mixing element, which is a rod or bar of some light transmissive material constructed such that internal reflection will trap the light down its length and long enough to accomplish thorough mixing.

The mixed light is then passed into a system of light detectors, each of which are adapted to measure one of the wavelengths of light representing a constituent element of the gases. A data processing unit records the total light count of each constituent element from each sample over a period of time. When the test is complete, each gas sample can be assigned a Raman-scattered "profile" from the data consisting of the ratios each of the constituent elements bear to each other. Since the constituency of the reference gas is known, the constituency of the unknown gas can be determined by comparison of its "profile" with that of the known.

The significant value being measured by the photomultiplier tubes, then, are the relative ratios of intensities that the various frequencies of Raman scattered light bear to each other in the reference gas and the sample gas. The individual intensities are only important when compared to those of the different frequencies of light from the same sample.

Any differences between the fiber optic networks leading into the mixing bar will show up equally in each tuned photodetector and cancel out as the *ratio* of the intensity of the various frequencies from a given gas will not be changed by the difference. Any differences between the bunched optical fibers bunches leading to the photomultiplier tubes will show up equally in each of the two gases and cancel out as the *comparative* ratios are what are used to define the relationship between the sample gas and the reference gas.

Gradual fluctuations in laser beam intensity are also harmless to the experiment as the same laser is simultaneously analyzing both gas samples. The chopper frequency is selected to insure that gradual changes in beam intensity and detection efficiency show up equally in both gas samples, optimally at a frequency of between 10 and 100 cycles per second.

Therefore, if exact knowledge of the constituency of a reference gas is known, the invention provides a reliable means of determining the constituency of a similar gas without complicated compensatory electronics, optics, or data processing. Much of the need for the compensatory apparatus in the prior art has been eliminated by the laser cavity configuration, which permits the samples to be viewed by the same beam, and the fiberoptic system, which permits the scattered light to be analyzed by the same detection system.

The principal need for data compiling equipment then is merely to work in conjunction with the choppers, so that the system will know which gas is being analyzed at a given time, and a system to measure the background noise measured by the detectors so that it will not be included in the data. The inventors have achieved an accuracy of one part in $10^6$ with this device.

It is the object of the present invention to provide a simple means of obtaining extremely reliable analyses of the constituency of various gases, such as in the comparison of air samples for the existence of pollutants or the depletion of oxygen.

It is another object of the invention to provide a means of stabilizing an intense laser beam through intracavity gas sample tubes.

Other objects and advantageous features of the invention will be apparent in a description of a specific embodiment thereof, given by way of example only, to enable one skilled in the art to readily practice the invention which is described hereinafter with reference to the accompanying drawings.

DESCRIPTION OF THE PREFERRED EMBODIMENT

Reference will now be made in detail to the present preferred embodiment of the invention, an example of which is illustrated in the accompanying drawings.

While the invention will be described in connection with a preferred embodiment, it will be understood that it is not intended to limit the invention to that embodiment. On the contrary, it is intended to cover all alternatives, modifications, and equivalents as may be included within the spirit and scope of the invention defined in the appended claims.

Figure 1:
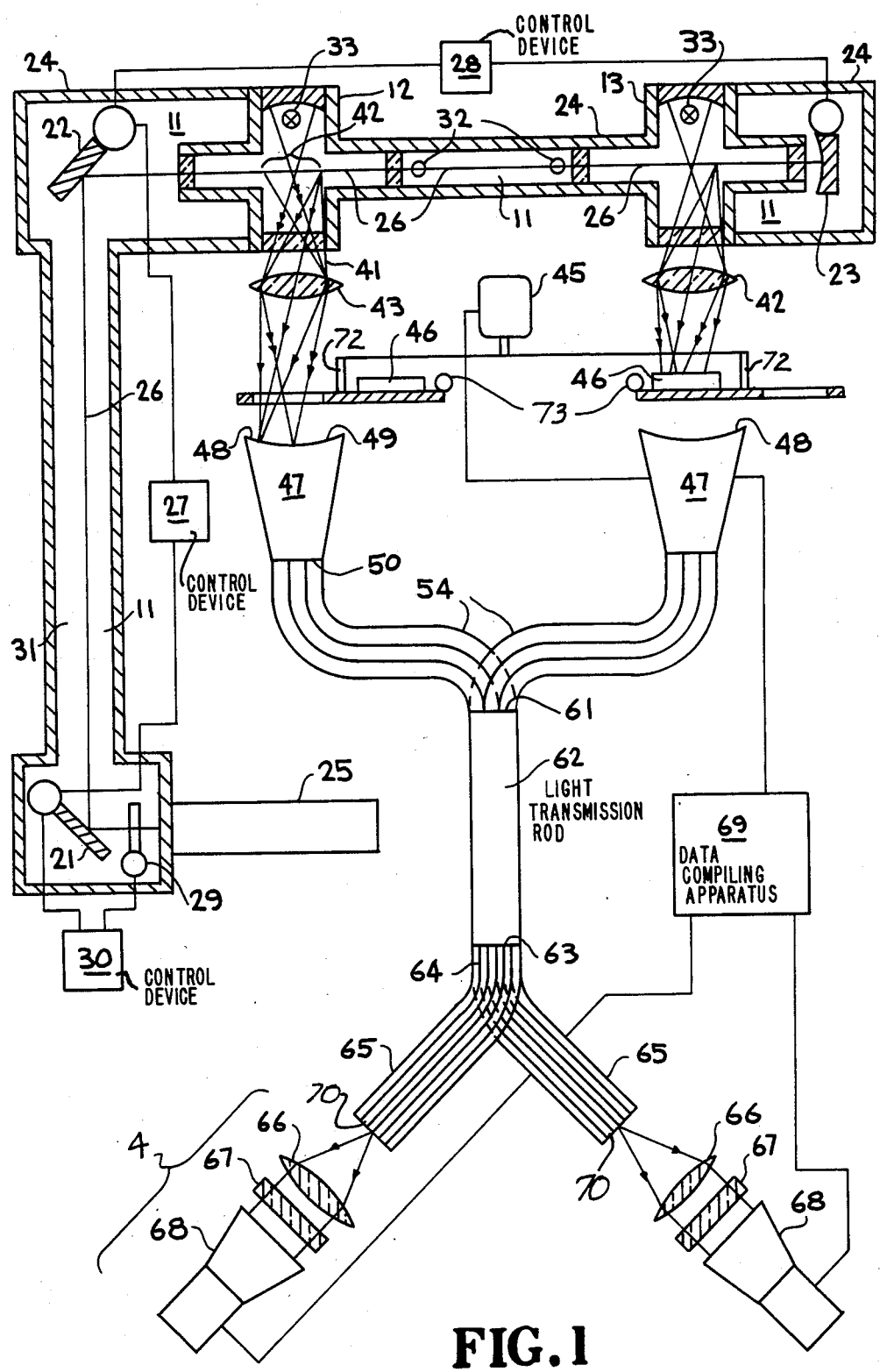
FIG. 1 is a schematic drawing of the preferred embodiment of the improved fiberoptic spectrophotometer.

A fiber optic gas analysis system according to the present invention is schematically shown in FIG. 1.

In order to provide an intense and stable laser beam 26 through the gas sample tubes 12, 13, the system involves a novel laser cavity 11 which is split into two functional regions 24, 25 as herein explained. A Spectra-Physics model 171-og model Argon laser, for example, has been used in the disclosed device, however other lasers may be used.

The laser cavity 11 is split into a Raman-scattering region 24, which is designed to house the gas sample tubes 12, 13, and a plasma discharge region 25 where the laser power is generated. The two regions are in optical communication via two adjustable coupling mirrors 21, 22 and a beam path 31. Mirror 23 is also adjustable and is the far mirror of the split laser cavity 11 configuration. The mirrors 21, 22, 23 thus operate to isolate the Raman-scattering region 24 from the optical effects of the plasma discharge region 25, where the laser power is generated and to separately control the beam 26 through each of these regions.

Monitoring devices 32 monitor the position of the beam 26 through the Raman-scattering region of the laser cavity 11. Control device 28, operably connected to monitors 32, then adjusts mirrors 22 and 23 simultaneously to achieve proper translation of the beam 26 through this region 24. Control device 27, also operably connected to monitors 32, then simultaneously adjusts mirrors 21 and 22 to properly tilt the beam 26 through this region 24. Monitoring device 29 monitors laser intensity. Control device 30 is operably connected to monitoring device 29 and adjusts mirror 21 to achieve peak laser power output from the plasma discharge region 25 of the laser cavity 11.

Figure 2:
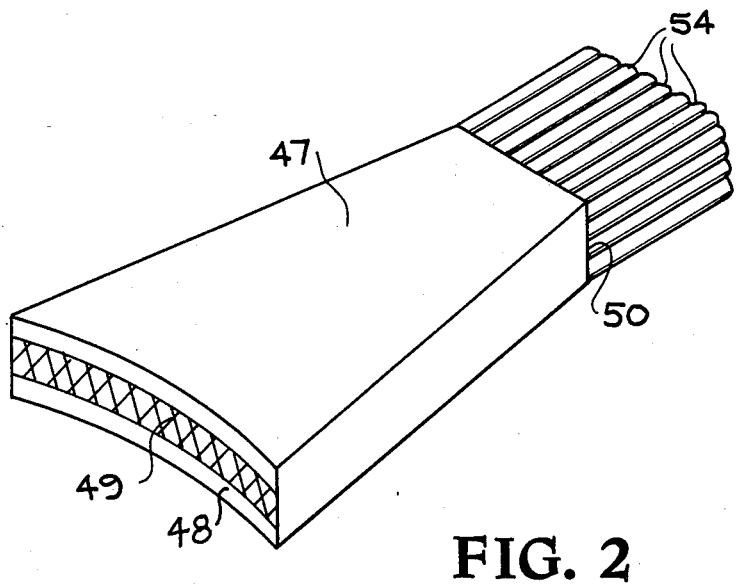
FIG. 2 is a drawing of the light transmissive sheet showing the curved input surface and the output optical fiber bundles.

Valves 33 permit the gas sample tubes 12, 13 to be filled with two similar gases. The constituency of one these gases, the reference, must be very accurately known and can be placed in either tube (12 or 13). The gases should be pumped into the tubes 12, 13 at a high pressure. As the laser beam passes through the two tubes 12, 13, Raman scattered light 41 radiates from the gases within the tubes. This Raman-scattered light 41 from each tube is emitted along a horizontal line which is the length of the laser path through the sample and is captured by separate identical respective focusing lens 42 and 43 where they are focused into a narrow line 49 onto the edge 48 of separate light transmissive sheets 47 as depicted in FIG. 2.

Choppers 46 are positioned between each of the focusing lens 42 and 43 and the input edge 48 of the light transmissive sheets 47. The choppers 46 are driven by a pair of tuning forks 72. The tuning forks 72 are driven by a motor 45 which is operably connected to monitors 73. The monitors 73 and motor 45 are adapted to ensure that the tuning forks 72 remain one half cycle out of phase so that the Raman-scattered light 41 from only one sample 12 or 13 at a time can be passed to its respective light transmissive sheet 47. Since the choppers 46 and tuning forks 72 are identical they will pass equal amounts of light in equal times if so controlled.

Figure 4:
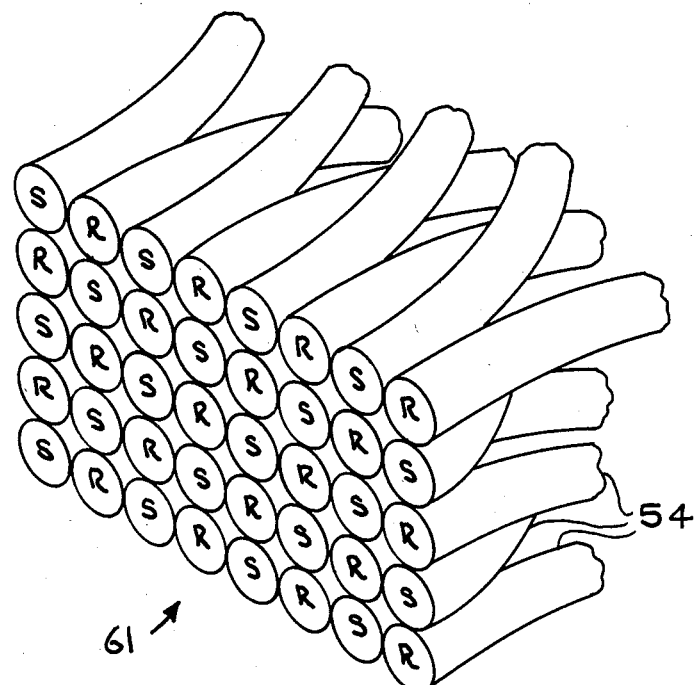
FIG. 4 is a drawing of the output interface surface of the optical fiber bundles showing the checkerboard array of bundles originating from either the reference or sample gas tube.
Figure 3:
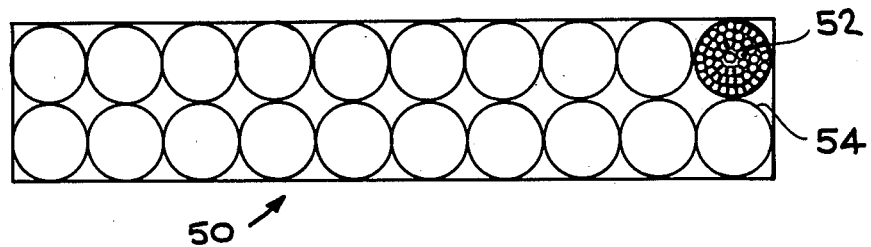
FIG. 3 is a drawing of the input interface of the optical fiber bundles with the output surface of the light transmissive sheet further showing an arrangement of bundled optical fibers.
Figure 6:
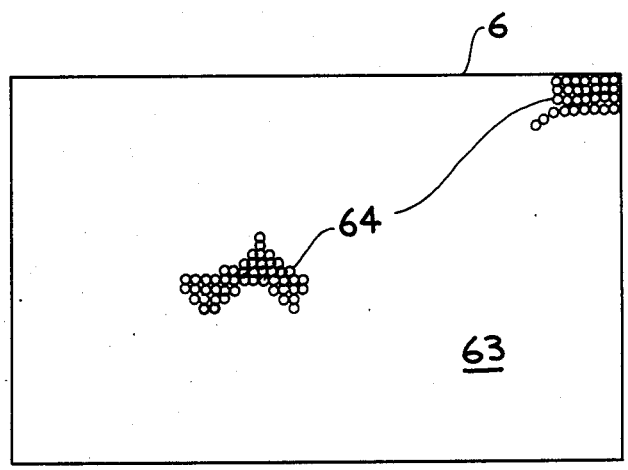
FIG. 6 is a drawing of the input interface of the individual output fibers with the output end of the mixing rod.
Figure 5:
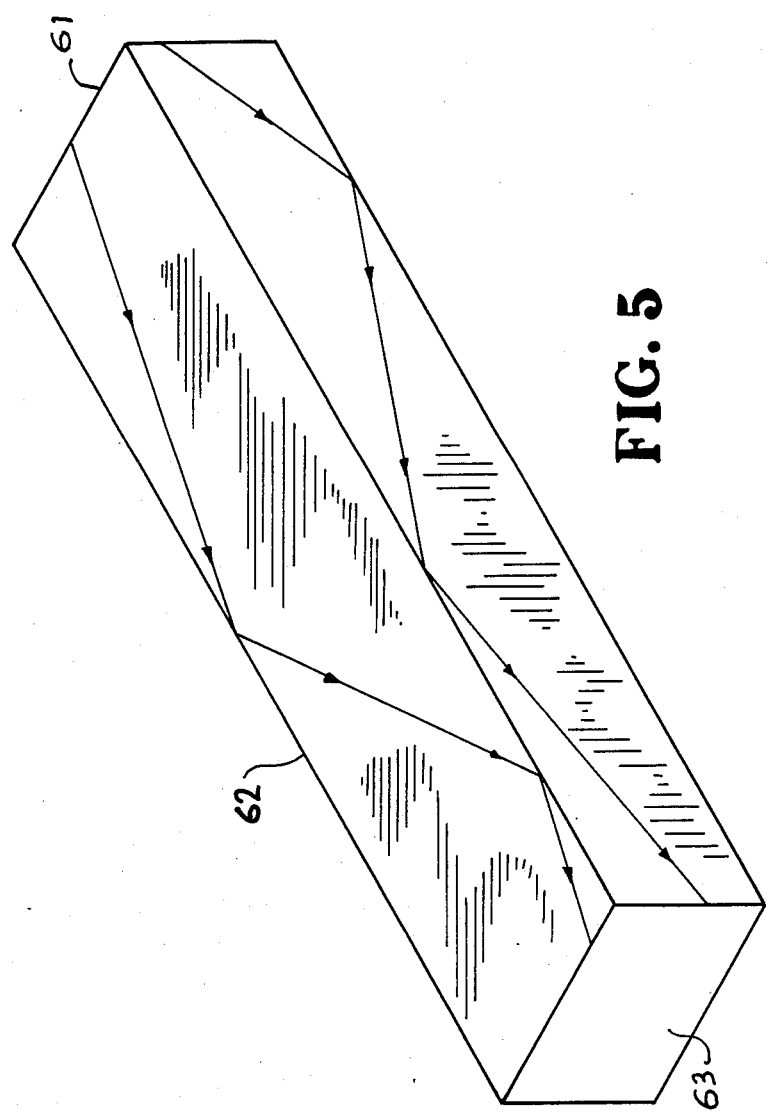
FIG. 5 is a drawing of the mixing rod further showing light rays kept within by internal reflection at its surface.

The input edges 48 of these light transmissive sheets 47 are curved such that the focused line of light 49 hitting all points on its surface will converge and mix down its length. At the output end 50 of each light transmissive sheet 47 the light is passed into an identical array of optical fibers 52, which are fused into a number of bundles 54 as depicted in FIG. 3, and bent such that they interface together the input end 61 of a light transmissive rod 62 in an alternating checkerboard type arrangement, as depicted in FIG. 4. The light is then transmitted down the length of this light transmissive mixing rod 62. The light transmissive rod 62 is long enough (as depicted in FIG. 5) so that the light, upon reaching the output end 63 is thoroughly mixed with the light from all of the optical fibers. The range of angles at which light is input into the rod 62 through the input end 61 is such that all the light transmitted into it from the optical fiber bundles is kept within by total internal reflection.

The output end 63 of the light transmissive rod 62 transmits the mixed light into numerous individual optical fibers 64 which interface the output end 63 of the rod 62 so as to maximize the effective transmission of light from the light transmissive rod 62. These optical fibers 64 are not fused together in any manner and can be divided into any number of individual bunches 65 of any number of fibers 64. As shown in FIG. 1 these output fibers 64 should be carefully divided into the bunches 65 such that each bunch 65 originates from all parts of the output face 63 of the light transmissive rod 62.

The free end 70 of each of these bunches 65 directs the light into one or more respective identical output collimating lens 66. The light is collimated into respective band pass filters 67 which are selectively tuned to pass a narrow band of Raman scattered light 41 representing a constituent of the gas sample 12 or 13 presently passed by one of the choppers 46. This filtered light is then passed into respective photo multiplier tubes 68 for measurement. There should, then, be one light detection system 74, including a bunch of optical fibers 65, collimating lens 66, band pass filter 67, and photomultiplier tube 68 for each constituent of the gases relevant to the analysis.

A data compiling apparatus 69 is operably connected to the photomultipliers 68 and the chopper monitors 73.

The data compiler 69 records the total light count through each of the photomultiplier tubes 68 over a sustained period of time as a function of which chopper 46 passed the Raman-scattered light 41. It also records the light counts produced when both choppers 46 are closed so that the "noise" in the system may be subtracted from the raw totals of light measured by the photomultiplier tubes 68. Four or more hours may be required to produce very accurate results in weak mixtures. However, adequately precise results are generally obtained within a half hour of testing with typical gas mixtures. At the end of the analysis a total light count for each constituent element (represented by a different photomultiplier tube 68) from each sample (12 or 13) is provided.

In the case of testing air samples, two constituent elements, nitrogen and oxygen, may be evaluated. At the end of the test four relevant totals would be produced $O_k$ (oxygen from the known, or reference sample), $N_k$ (nitrogen from the known, or reference sample), $O_u$ (oxygen from the unknown sample), and $N_u$ (nitrogen from the unknown sample). Since the constituency of the reference air (or $A_k$) is known, the constituency of the unknown air (or $A_u$) may be determined by comparing the ratios $O_k/N_k$ and $O_u/N_u$.

As it is the ratios, rather than the totals, which are important, the system has a degree of flexibility not present in previous spectrophotometer art. For instance, since the Raman-scattered light from oxygen is much weaker than nitrogen in air samples, the bunched optical fibers 65 selected to pass light into the oxygen-biased band pass filter (either of 67) may consist of a greater number of individual optical fibers 54 than the bunch 65 passing light to the nitrogen-biased filter (the other of 67)

The primary advantage, however, is in the simplification of the data compiling arrangement made possible by the inherent cancelling out of experimental errors. Only raw totals, rather than averages, variances, or units/time need be carefully recorded. The control mechanisms and monitors utilized (such as 27, 28, 29, 30, 32, and 73) are designed merely to stabilize the system rather than to provide data or feedback to the compilers.

Described, then, is a simple apparatus for providing accurate comparison of the relative constituency of an unknown gas sample with that of a known gas sample without the need for complicated compensatory electrical, optical, and data compiling equipment.

While embodiments of the invention have been shown and described, further embodiments or combinations of those described herein will be apparent to those skilled in the art without departing from the spirit of the invention. For instance, although primarily designed for one unknown and a reference, more than one unknown sample could be placed within the cavity with the reference. A more elaborate chopping system and input fiber optic system would be required to channel the Raman-scattered light into the mixing element. Also, solid state photodiodes could easily be substituted for the photomultiplier tubes. Additionally, the individual optical fibers 54, could be divided into any number of bunches 65 leading to an equal number of light detection systems 74 (consisting of a focusing lens 66, band pass filter 67, and photomultiplier tube 68) in order to test for numerous constituent elements.

We claim:

1. A method for analyzing the relative composition of two similar gases, including the steps of:

passing an intense laser beam through samples of each of the two gases, the composition of one of which is accurately known, for producing a band of Raman-scattered light from each;

alternately directing each of the bands of Raman-scattered light from each gas through a common light-mixing system so that all wavelengths present in the Raman-scattered light from each sample will be mixed spatially in a thorough manner;

directing the mixed Raman-scattered light to light detection systems each of which is tuned to measure a particular wavelength of light representing the presence of and relative amount of a constituent element of the gas sample;

comparing a ratio of constituent elements present in the known gas sample to that of the unknown gas sample; and determining the relative amounts of each constituent element of the unknow gas by comparing the relationship of an amount of Raman-scattered light from a constituent in the unknown gas sample to the amount of Raman-scattered light from the other constituents in the unknown gas sample with the relationship of an amount of Raman-scattered light from a constituent in the known gas sample to the amount of Raman-scattered light from the other constituents in the known gas sample.

2. A method for stabilizing the position and maximizing the power of a laser beam through samples of a material placed within a laser cavity, including the steps of:

using a plurality of adjustable mirrors for dividing the laser cavity into a plasma discharge region and a gas sample region;

controlling certain of the adjustable mirrors which couples the plasma discharge region of the laser cavity with the gas sample region of the cavity to achieve proper translation of the beam through the samples;

separately controlling adjustable mirrors located at either end of the gas sample region of the cavity to achieve proper tilt of the beam through the gas samples; and separately monitoring and controlling one of the adjustable mirrors located at one end of the plasma discharge region of the cavity to achieve peak laser power output.

3. An apparatus for analyzing the relative composition of two similar gases, comprising;

a laser means in which a laser beam is passed through at least two similar gas samples so as to create an associated band of Raman-scattered light from each said gas sample;

said gas samples being contained in associated individual transparent gas sample tubes, said gas sample tubes being constructed to house said gas samples at high pressure and isolate said gas samples from an atmosphere within said laser means;

a focusing means for focusing each of said bands of Raman-scattered light from each said gas sample tube to separate fiber optic input systems, said fiber optic input systems comprising a light converging means and an equal number of similar fused optical fiber bundles;

a means for chopping each said focused bands of Raman-scattered light from each said gas sample such that said bands of Raman-scattered light from one said gas sample may enter its said associated fiber optic system at a given time, said chopping means being operably connected to an associated recording means;

a fiber optic network comprising an arrangement of said optical fiber bundles in which the bundles transmitting the Raman-scattered light from one of said gas samples is equally interwoven with the optical fiber bundles transmitting Raman-scattered light from an other said gas samples;

an optical mixing element into which the said Raman-scattered light from each said gas sample from said fiber optical network is fed and in which said Raman-scattered light from each gas sample is thoroughly mixed;

an output means composed of groups of optical fibers connected to said optical mixing element through which the said mixed Raman-scattered light is divided into numerous individual output optical fibers;

a light detection and measuring means for each wavelength present in the said Raman-scattered light from each said gas samples connected to said output means, and into which a bunched group of said output optical fibers directs said mixed Raman-scattered light from said optical mixing element to an associated light detection and measuring means;

each said light detection and measuring means being operably connected to a recording means, and said recording means being constructed to display and record which sample of said Raman-scattered light is passed through said chopping means and the amount of light measured by each said light detection and measuring means over a period of time.

4. The apparatus described in claim 3 in which said laser means comprises;

a laser cavity which further comprises two separate regions, a first of said regions comprising a laser plasma discharge region and a second of said regions comprising a sample region containing said gas sample tubes;

said plasma discharge region further comprising an adjustable discharge mirror located at one end for directing a laser beam towards an associated adjustable near mirror located at a near end of said sample region, said near mirror directing the laser beam through said gas sample tubes;

said sample region further comprising an adjustable far mirror located at an end farthest from said discharge region for directing said laser beam back towards said near mirror and back through said gas sample tubes;

said near mirror being generally oriented to reflect said laser beam reflected from said discharge mirror toward said far mirror and through said gas samples and to reflect said laser beam reflected from said far mirror to said discharge mirror;

said discharge mirror and said near mirror being operably connected through a control means for simultaneous adjustment which prevents translational drift of said laser beam through said gas sample tubes;

said near mirror and said far mirror being operably connected through a control means for simultaneous adjustment to ensure proper tilt of said laser beam through said gas sample tubes; and said discharge mirror being operably connected to an associated power feedback means for further adjustment to insure peak power of said laser beam.

5. The invention described in claim 3, said chopping means, further comprising;
a shutter located between each said focused line image of Raman-scattered light and each of said separate fiber optic systems, said shutter having an aperture large enough to pass an associated strip of Raman-scattered light; and
said shutters being operably connected to identical tuning forks having a resonant frequency of between ten and one hundred cycles per second, each said tuning fork further being operably connected to and driven by an associated motor;
said motor being in control communication with a computer processing unit; and
said computer processing unit being constructed to control said motor to ensure that only one of said shutters is open at a given time and that said shutters operate at consistent and equal periods and to record which said shutter is open at a given time.

6. The invention described in claim 3 in which each said light converging means further comprises;
a light transmissive sheet having an input end which is shaped to direct all the said Raman-scattered light focused upon its surface down its length in a converging manner to an associated output end, and having a thickness wider than said strips of focused, Raman-scattered light, and a tapered shape from said input end to an output end,
said output end being in maximum optical communication with numerous optical fibers; and
said optical fibers being arranged in identical optical fiber bundles.

7. The invention described in claim 3 in which said fiber optic network further comprises;
said fused optical fiber bundles from each fiber optical system bent into an alternating array in which each said fused optical fiber bundle from one said fiber optical system is adjacent on all sides with said fused optical fiber bundles from other said fiber optic input systems;
said alternating array being arranged to evenly spread the said fused optical fiber bundles from each said fiber optic input system; and
said alternating array of said optical fiber bundles further establishing maximum optical communication between each said fused optical fiber bundle and the input end of said optical mixing element.

8. The invention described in claim 3, in which said optical mixing element further comprises;
a bar of a light transmissive substance having an index of refraction such that said transmitted Raman-scattered light from said fiber optical network will be confined within said bar by total internal reflection; and
said bar being of such length as to insure thorough mixing of said transmitted Raman-scattered light passing through said bar from said fused optical fiber bundles to said individual optical fibers.

9. The invention described in claim 3 in which each said light detection and measuring means further comprises;
a collimating means with lens large enough to gather all said Raman-scattered light transmitted through each said bunch of individual optical fibers and collimate said gathered Raman-scattered light into an associated band pass filter;
each said band pass filter being selected to pass a narrow band of the Raman-scattered light corresponding to one associated constituent element of said gas sample into an associated photomultiplier tube; and
said photomultiplier tube being adapted to detect and measure said filtered light passed into it.

10. The invention described in claim 3 in which the number of said gas sample tubes is two.

11. The invention described in claim 4 in which the number of said gas sample tubes is two.

12. The invention described in claim 5 in which the number of said gas sample tubes is two.

13. The invention described in claim 6 in which the number of said gas sample tubes is two.

14. The invention described in claim 7 in which the number of said gas sample tubes is two.

15. The invention described in claim 8 in which the number of said gas sample tubes is two.

16. The invention described in claim 9 in which the number of said gas sample tubes is two.

* * * * *